US 8,795,599 B2

(12) United States Patent
Fontcuberta et al.

(10) Patent No.: US 8,795,599 B2
(45) Date of Patent: Aug. 5, 2014

(54) ARRANGEMENT FOR STERILISING OBJECTS BY ELECTRON BOMBARDMENT

(75) Inventors: Philippe Fontcuberta, Vendome (FR); Didier Morisseau, Antony (FR)

(73) Assignee: Linac Technologies S.A.S., Orsay (FR)

( * ) Notice: Subject to any disclaimer, the term of this patent is extended or adjusted under 35 U.S.C. 154(b) by 1196 days.

(21) Appl. No.: 11/911,161

(22) PCT Filed: Apr. 19, 2006

(86) PCT No.: PCT/FR2006/050353
§ 371 (c)(1),
(2), (4) Date: Oct. 10, 2007

(87) PCT Pub. No.: WO2006/111681
PCT Pub. Date: Oct. 26, 2006

(65) Prior Publication Data
US 2008/0193341 A1    Aug. 14, 2008

(30) Foreign Application Priority Data

Apr. 19, 2005   (FR) ...................................... 05 50987

(51) Int. Cl.
*B01J 19/08*    (2006.01)
(52) U.S. Cl.
USPC ..... 422/186; 422/22; 204/157.15; 250/492.1; 250/492.3; 250/455.11
(58) Field of Classification Search
CPC ............................ A61L 2/087; A61L 2202/23
USPC ............. 422/186, 22; 204/157.15; 250/492.1, 250/492.3, 455.11
See application file for complete search history.

(56) References Cited

U.S. PATENT DOCUMENTS

| 5,053,196 A * | 10/1991 | Ide et al. .......................... 422/28 |
| 5,279,788 A * | 1/1994 | Kudo et al. ...................... 422/21 |
| 2005/0230640 A1* | 10/2005 | Loda et al. ............... 250/455.11 |
| 2006/0186350 A1 | 8/2006 | Fontcuberta et al. |

FOREIGN PATENT DOCUMENTS

| DE | 39 11 749 A1 | 10/1989 |
| DE | 102 35 375 A1 | 2/2004 |
| EP | 0 401 775 A2 | 12/1990 |
| EP | 1 340 512 A1 | 9/2003 |
| JP | S58-112928 | 7/1983 |
| JP | H08-184700 | 7/1996 |
| JP | 2000-128131 | 5/2000 |
| JP | 2004-191307 | 7/2004 |
| WO | WO 99/39750 | 8/1999 |

OTHER PUBLICATIONS

Sadat et al "E-Beam—a new tranfer system for isolator technology", Radiatio Physics and Chemistry, 63 (2002) p. 587-589.*

* cited by examiner

*Primary Examiner* — Xiuyu Tai
(74) *Attorney, Agent, or Firm* — Oblon, Spivak, McClelland, Maier & Neustadt, L.L.P.

(57) ABSTRACT

A facility (1) for sterilizing objects by electron bombardment includes a first conveyor and a second conveyor which are used for transporting objects and placed on either side of a treatment chamber. The facility is provided with an input rotatable conveyor designed for moving said objects and located between the first conveyor and the chamber, and an output rotatable conveyor also designed for displacing objects and located between said chamber and the second conveyor.

13 Claims, 5 Drawing Sheets

ARRANGEMENT FOR STERILISING OBJECTS BY ELECTRON BOMBARDMENT

TECHNICAL FIELD

The present invention relates in general to the field of sterilizing objects by electron bombardment, this bombardment possibly being of the low-energy type for treatment of the outer surface of these objects, or of the type having more significant energy in order to treat the core of these objects.

It is particularly but not exclusively applicable to sterilization by electron bombardment of objects having a substantially rectangular parallelepiped shape, such as objects called "tubs" corresponding to closed containers holding a multitude of elements that have preferably been chemically pre-sterilized, such as medical syringes, for example.

STATE OF THE PRIOR ART

Facilities enabling sterilization of objects having substantially rectangular parallelepiped shapes by low-energy electron bombardment, i.e. with an energy lower than approximately 400 keV, are known from the prior art.

To do this, these facilities typically comprise three low-energy accelerator/gun-type sources of approximately 200 keV, and are arranged at 120° from each other around a treatment chamber through which the objects are moved translationally in order to be treated. In this way, during its continuous passage through the treatment chamber, the outer surface of each object is simultaneously illuminated over 360° by the combination of the three electron beams respectively coming from the aforementioned sources, which have been carefully positioned.

This type of facility has proved to be satisfactory, particularly due to its effectiveness related to the slight penetration of the electron beam and the sporicidal effect produced, and also due to the rapidity of treatment as well as the safety provided.

Nevertheless, this facility has a non-negligible drawback residing in the fact that it has a treatment chamber, within which the path of the object is relatively complex, for example U-shaped, so as to provide biological protection against to the electron beams emitted by the various sources of the sterilization means. Indeed, in such a case where the treatment chamber is defined by two stainless steel walls located on both sides of the path and each extending all along the U, the sterilization means are found at the base of the U, while the branches of this U are intended to be long enough to ensure that the radiations do not propagate beyond the open ends of these two branches through which the objects are intended to pass. On this account, it may be noted that the two open ends of the U may be likened to the inlet and outlet of the treatment chamber, on either side of which are found a first conveyor used to bring objects into this chamber, as well as a second conveyor, respectively, ensuring the removal of the treated objects toward a production isolator.

Thus, the complex shape of the treatment chamber and the path of the object imposed by biological safety measures makes the bulkiness of the facility particularly substantial, such that it is therefore not entirely optimized. Moreover, it is consequently necessary to provide curved conveyors in the treatment chamber, the complexity and cost of which are greatly increased relative to traditional rectilinear conveyors

OBJECT OF THE INVENTION

The object of the invention is therefore to propose a facility for sterilizing objects by electron bombardment at least partially resolving the abovementioned drawbacks relative to the prior art.

To do this, the invention relates to a facility for sterilizing objects by electron bombardment, comprising sterilizing means able to generate at least one electron beam along an axis passing through a treatment chamber of the facility within which the objects are intended to be set into motion, the facility comprising a first conveyor as well as a second conveyor designed for moving objects and placed on either side of the treatment chamber. According to the invention, the facility is provided with an input rotatable conveyor used for transporting objects and placed between the first conveyor and the treatment chamber, and an output rotatable conveyor also used for transporting objects and placed between this treatment chamber and the second conveyor, the aforementioned rotatable conveyors being used and placed so as to provide a barrier for the radiations emitted by the sterilization means.

It may be understood that one particularity of the invention resides in the fact of providing two rotatable conveyors intended to be set into rotation in order to transport objects, and respectively provided upstream from the inlet of the treatment chamber, and downstream from the outlet of this chamber. This therefore provides a barrier for the radiations emitted by the source(s) of the sterilization means, such that the treatment chamber no longer has to be made according to a complex shape such as those encountered in achievements of the prior art.

The facility for sterilizing objects may therefore advantageously have reduced bulk, for example by providing a rectilinear path for the object inside the treatment chamber, while providing satisfactory biological protection against the electron beam(s) emitted by the various sources of the sterilization means.

Preferably, each rotatable conveyor has multiple radial projections arranged such that any two of them, directly consecutive to each other, define a housing to receive an object, this object being able to be moved in the housing when the conveyor is set into motion, causing rotation of this housing. It is essentially these radial projections, for example four in number, which provide a biological protection barrier against the electron beam(s), both at the inlet and outlet of the treatment chamber.

Preferably, the facility comprises a first transfer means making it possible to transport an object located at a downstream end of the first conveyor, into a housing of the input rotatable conveyor laid out facing this downstream end of the first conveyor. Thus, once the object is located inside the aforementioned housing, the input conveyor may be set into rotation so as to move this object into a position enabling it to be introduced in the treatment chamber.

In this respect, it is noted that the facility comprises second transfer means making it possible to transport an object located in a housing of the input rotatable conveyor which communicates with an inlet of the treatment chamber, right up to the inside of this treatment chamber. Naturally, this housing which communicates with the inlet of the treatment chamber and in which is located an object to be treated corresponds to the same housing which was previously, before rotation of the input conveyor, laid out facing the downstream end of the first conveyor in order to receive the object coming from it.

Moreover, the facility comprises a third transfer means making it possible to move an object located inside the transfer chamber, into a housing of the output rotatable conveyor which communicates with an outlet of this treatment chamber. Consequently, once the object is located inside the housing just mentioned, the output rotatable conveyor may be set into rotation in order to move this object such that it is entirely extracted from the treatment chamber.

In this respect, it is noted that the facility comprises a fourth transfer means making it possible to move an object located in a housing of the output rotatable conveyor laid out facing an upstream end of the second conveyor, right up onto this upstream end of the second conveyor. Here again, it should be understood that the housing laid out facing the upstream end of the second conveyor corresponds to the same housing, which, before rotation of the output conveyor, was in communication with the outlet of the treatment chamber.

The treatment chamber is equipped with at least one internal conveyor making it possible to set the objects into motion inside this chamber, and preferably equipped with a primary internal conveyor onto which the objects may be brought by the second transfer means, and with a secondary internal conveyor from which the objects may be moved into a housing of the output rotatable conveyor, by the third transfer means.

In this configuration, which is particularly well-suited to cases where a plurality of sources each emitting an electron beam are implemented, it may be provided for the primary internal conveyor to have an upstream end located in proximity to the inlet of the treatment chamber, and for the secondary internal conveyor to have a downstream end located in proximity to the outlet of the treatment chamber.

Moreover, it is also provided for the downstream end of the primary internal conveyor to be located facing and away from an upstream end of the secondary internal conveyor, so as to form an inter-conveyor space able to be crossed by the electron beams of the sterilization means.

Preferably, the first conveyor, second conveyor, primary internal conveyor and secondary internal conveyor are each substantially rectilinear, and substantially arranged along a same straight line parallel to a direction of the forward motion of the objects. Thus, the object path inside the treatment chamber is rectilinear, which provides relatively small bulkiness. Moreover, although it was preferably provided to equally align the first and second conveyors placed on either side of this chamber, these may nevertheless be arranged differently, without departing from the scope of the invention. As an illustrative example, the first conveyor may be arranged at 90° relative to the primary internal conveyor, and likewise, the second conveyor may also be arranged at 90° relative to the secondary internal conveyor. This ability to modify the positioning of the first and second conveyors is naturally achieved by the presence of input and output rotatable conveyors, for which it is only necessary to modify the range of the rotations to be able to adapt to the various layouts of the conveyors.

As previously stated, the sterilization means comprise a plurality of sources each generating an electron beam along an axis passing through the treatment chamber, and preferably three sources respectively generating three electron beams along axes arranged respectively at 120° relatively to each other, in a plane P orthogonal to a direction of forward motion of the objects.

In this preferred solution which is particularly adapted to providing "surface" treatment, sterilization consists of achieving low-energy electron bombardment on the surface of the objects. Thus, as it continuously passes through the treatment chamber, at the inter-conveyor space, the outer surface of each object is simultaneously illuminated over 360° by the combination of the three electron beams respectively resulting from the aforementioned sources, which have been carefully positioned. In this respect, it is obviously specified that this is possible by providing that the plane P crosses the inter-conveyor space.

Also preferentially, the sources are laid out such that each of the three axes passes through an object to be treated placed at this inter-conveyor space.

Naturally, this solution with three sources or more may also be considered to provide a "core" treatment, according to which sterilization consists of achieving a stronger energy electron bombardment on the objects, the power then being able to be greater than 400 keV, and reaching 5 or even 10 MeV. Naturally, for the core treatment, the number of sources may be decreased or increased as needed, and is therefore not limited to three.

The present invention also covers a facility whereof the sterilization means would be solely made up of only one source able to generate a single electron beam. This solution is recommended in the framework of a core treatment of the objects, and advantageously does not require providing for several internal conveyors within the treatment chamber.

Preferably, the second conveyor opens into a production isolator into which the sterilized objects are transported.

It is noted that with the invention it is also possible to perform a core treatment of objects packaged in their final packaging. In this type of case, the second conveyor opens into a production isolator, or into another protected environment, as the packaging itself protects the product after treatment.

Preferably, the input rotatable conveyor is placed in a crown having an opening facing the first conveyor so that it may allow the introduction of objects into the input rotatable conveyor, and an opening located in the extension of the inlet of the treatment chamber and upstream therefrom. Similarly, the output rotatable conveyor is placed in a crown having an opening located in the extension of the outlet of the treatment chamber and downstream therefrom, and an opening located facing the second conveyor so as to allow extraction of the objects from the output rotatable conveyor.

It is noted that these two crowns are each simultaneously used for providing a barrier against the radiations emitted by the beams, and for avoiding removal of the objects located in the housings of the rotatable conveyors, when the latter are set into rotation.

Lastly, as stated above, it should be noted that the facility is made so as to allow surface or core treatment of the objects to be treated.

Other advantages and characteristics of the invention will appear in the detailed and non-limiting description below.

BRIEF DESCRIPTION OF THE DRAWINGS

This description will be made with regard to the appended drawings, wherein.

DETAILED DESCRIPTION OF PREFERRED EMBODIMENTS

Figure 1:
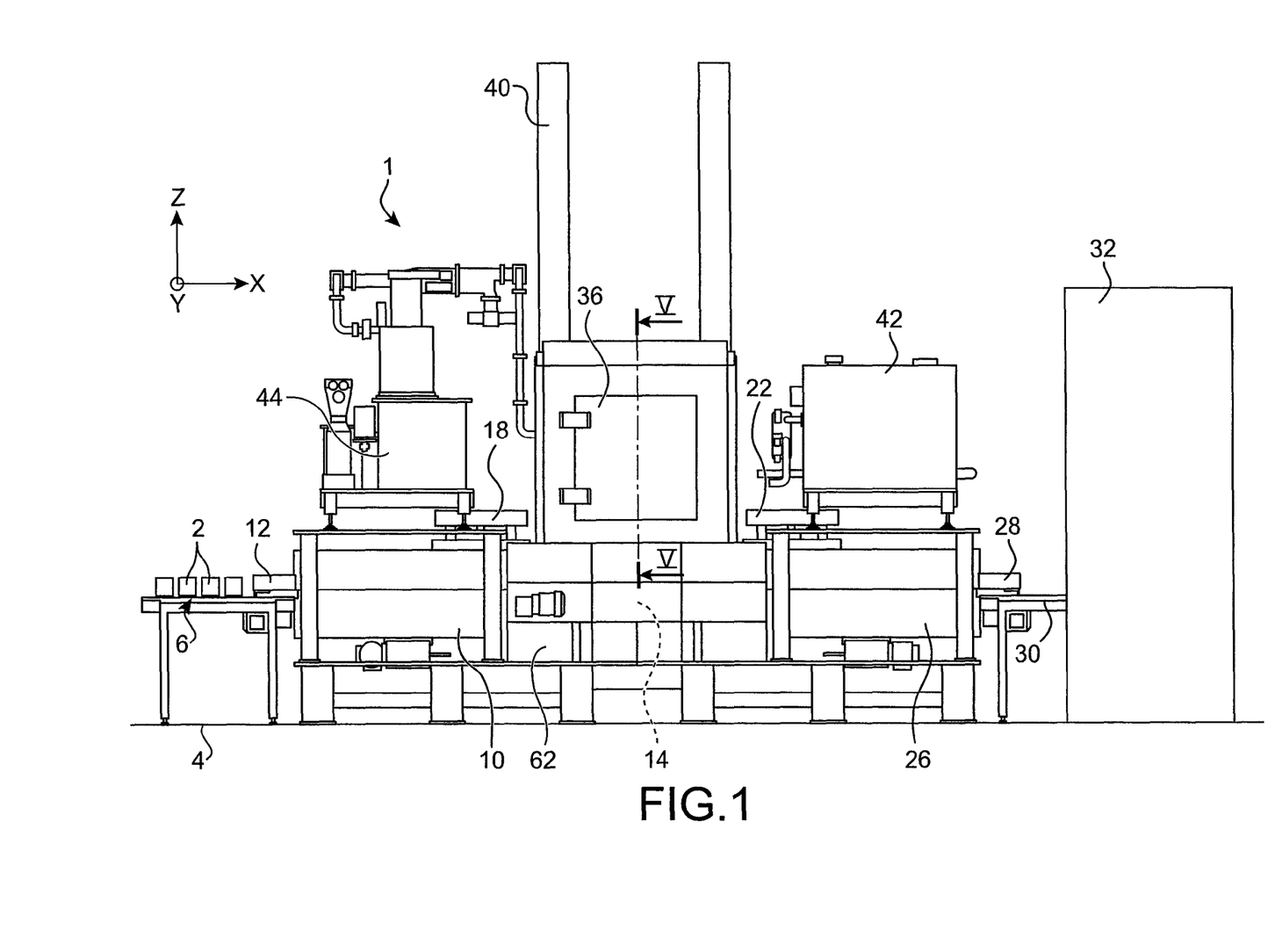
FIG. 1 shows a front view of a facility for sterilizing objects by electron bombardment, according to a preferred embodiment of the present invention.
Figure 2:
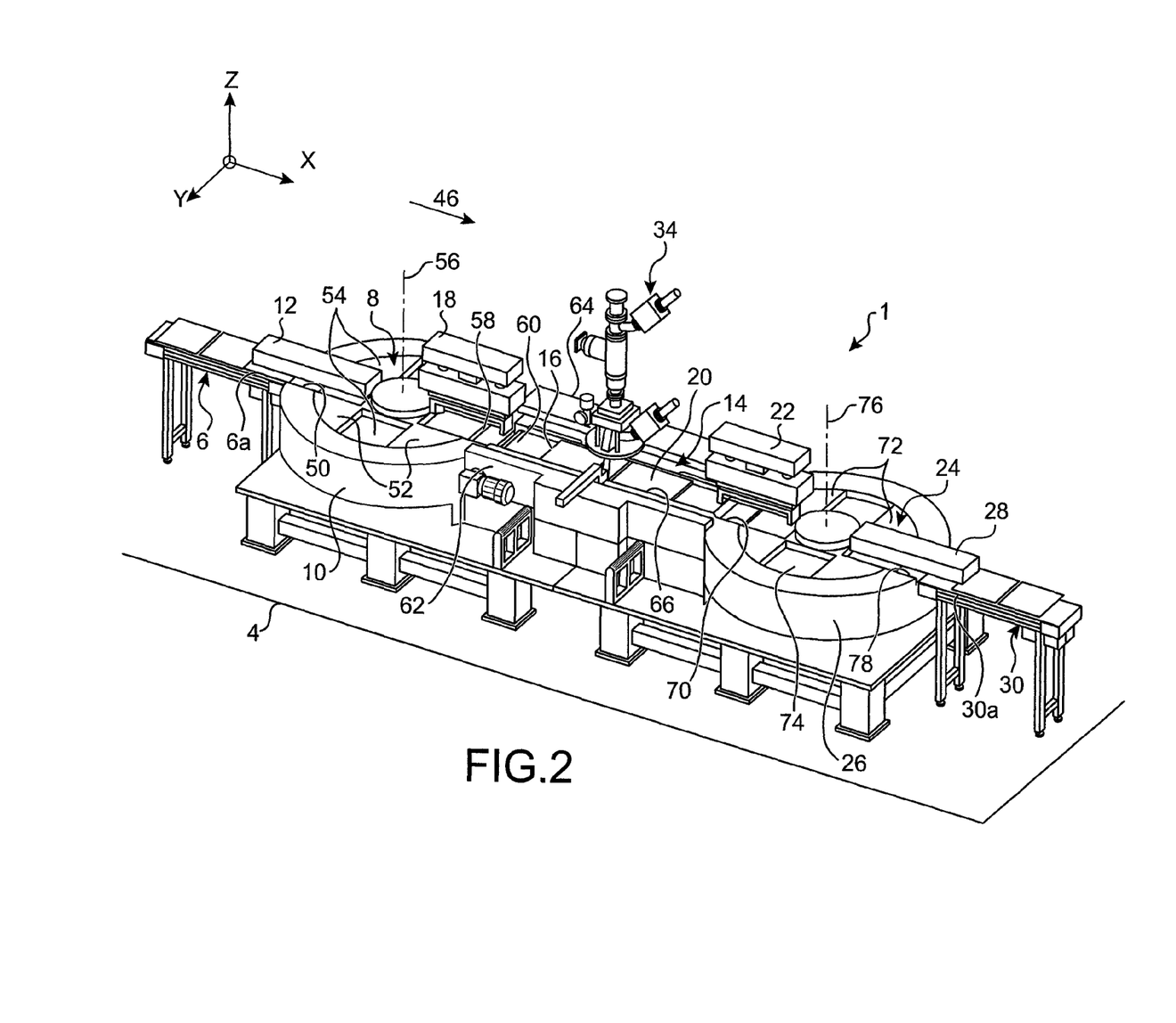
FIG. 2 shows a partial perspective view of the facility shown in FIG. 1, the objects to be treated having been voluntarily omitted from the illustration for reasons of clarity.

With reference first to both FIGS. 1 and 2, a facility 1 for sterilizing objects 2 by electron bombardment may be seen, this facility 1 being preferably but not exclusively intended for the treatment of objects having a substantially rectangular parallelepiped shape. Moreover, even though the application described hereafter concerns the surface treatment of the objects to be sterilized, it may naturally be applied for core treatment of the latter.

As previously stated, this object shape corresponds in particular to that of tubs holding a multitude of elements that have preferably been chemically pre-sterilized, such as medical syringes, for example one hundred of them per tub.

The facility 1 rests on a floor 4, which may be likened to a horizontal plane. On this account, it may be noted that the description will be made with reference to a direction X parallel to the floor 4 and corresponding to a direction of forward motion of the objects within the facility, a direction Y corresponding to a transverse direction of the facility also parallel to the floor 4, as well as a direction Z corresponding to a height direction which is orthogonal to this same floor 4, the directions X, Y and Z being orthogonal to each other.

Overall, the facility comprises the following elements: a first conveyor 6, an input rotatable conveyor 8 placed in a crown 10, a first object transfer means 12, a treatment chamber 14 in which are located a primary internal conveyor 16 cooperating with a second object transfer means 18 as well as a secondary internal conveyor 20 cooperating with a third object transfer means 22, an output rotatable conveyor 24 placed in a crown 26, a fourth transfer means 28, and a second conveyor 30 opening into a production isolator 32.

On the other hand, this facility 1 also comprises sterilization means 34 which will be described in detail later on, with reference to FIG. 5, and which have the particularity on the one hand of producing at least one electron beam within the treatment chamber 14, and on the other hand of being enclosed in a shielded casing 36 as shown in FIG. 1. As an indication, the shielded casing 36 may be made of lead with a thickness of approximately 15 mm within the framework of low-energy treatment (approximately 200 keV), or approximately 600 mm within the framework of higher energy treatment (for example, of the order of 5 MeV).

The facility 1 also has two pipes 38, 40 communicating with the treatment chamber 14 and being used for bringing in fresh air, and removing the ozone produced by the electron bombardment, respectively.

On the other hand, cooling means 42 as well as a klystron 44 connected to the sterilization means 34 are also provided on the facility 1.

More particularly with reference to FIG. 2, a direction of forward motion of the objects 46 within the facility 1 is shown, which is parallel to the direction X. The four conveyors 6, 16, 20, 30 are preferably straight/rectilinear and aligned along this direction 46, as clearly visible in this FIG. 2.

The first conveyor 6 is a gravity roller conveyor (or of another suitable type) ensuring automatic displacement of the objects 2 to be treated, substantially along the direction X. It has a downstream end 6a located above and facing an opening 50 formed in the crown 10 to allow the passage of the objects 2, and allows the introduction of these objects into the input conveyor 8. In this respect, for the same reason as for certain other elements of the facility 1 which will be described hereafter, this crown 10 is preferably and primarily made of lead essentially for the purpose of providing complete biological protection against the electron beams emitted by the sterilization means 34 during treatment.

Inside this crown 10, the input rotatable conveyor 8 is located which has a plurality of radial projections 52, preferably four and primarily in lead, laid out such that any two of them directly consecutive to each other define a housing 54 to receive an object 2. As this may be seen in FIG. 2, the projections 52 defining four regularly distributed housings 54 may have a shape making it possible to define, two by two, substantially parallelepiped housings 54, having a shape which complements that of the objects 2, or that of an assembly of objects within the framework of a core treatment. Thus, each object 2 may then be set into rotation in one of the housings 54 along an axis 56 corresponding to the axis of rotation of the rotatable conveyor 8, when this same rotatable conveyor is moved rotationally. It is noted as an indication, that the vertical axis 56, also corresponding to the axis of the crown 10, the inner surface of said annulus 10 conforming with the shape of the free ends of the radial projections 52, is preferably located in a vertical plane parallel to the direction 46 and fictitiously crossing the four aligned conveyors, preferably in their middle.

At a downstream portion of the crown 10, the latter has another opening 58 which is located in the extension of an inlet 60 of the treatment chamber 14 and upstream therefrom, this opening 58 being diametrically opposite to the opening 50.

The treatment chamber 14 is defined by two walls 62, 64 primarily in lead, which are oriented according to planes XZ and which jointly define the inlet 60 as well as the outlet 66 of this chamber. Between these two walls 62, 64 providing biological protection, are located the two internal conveyors 16, 20, for which one upstream end 16a of the primary internal conveyor 16 is located in proximity to the inlet 60, and one downstream end 20a of the secondary internal conveyor 20 is positioned in proximity to the outlet 66.

Moreover, the downstream end 16b of the conveyor 16 and the upstream end 20b of the conveyor 20 are located facing each other, and are separated by an inter-conveyor space 68, the length of which along the X direction is set so as to be smaller than the length along this same direction of an object 2 to be treated placed on the internal conveyor 16, such that the relevant object may automatically pass from one internal conveyor to the other. The effect sought is in reality to be able to obtain a continuous feed of an object 2 from one end to the other of the treatment chamber 14 and solely with the help of two internal conveyors 16, 20 at regulated speeds, while also providing the inter-conveyor space 68 to allow the electron beams to illuminate the outer surface of this object 2 simultaneously over 360° when it passes above this space 68.

In the extension of the outlet 66 defined by the two parallel walls 62, 64, is located an opening 70 of the crown 26 in which the output rotatable conveyor 24 is located, the layout between the latter and the crown 26 made primarily of lead being substantially identical to the one described between the crown 10 and the input rotatable conveyor 8.

More specifically, the output rotatable conveyor 24 has a plurality of radial projections 72, preferably four and primarily in lead, laid out such that any two of them which are directly consecutive to each other define a housing 74 to receive an object 2. As this may be seen in FIG. 2, the projections 72 defining four regularly distributed housings 74 may have a shape which makes it possible to define, two by two, substantially parallelepiped housings 74, having a shape which complements that of the objects 2. In this way, each object 2 may then be set into rotation in one of the housings 74 along an axis 76 corresponding to the axis of rotation of the rotatable conveyor 24, when this same rotatable conveyor is set into motion. It is noted as an indication that the vertical axis 76, also corresponding to the axis of the crown 26, the inner surface of this crown 26 conforming with the shape of the free ends of the radial projections 72, is preferably located in the vertical plane fictitiously crossing the four aligned conveyors.

At a downstream portion of the crown 24, the latter has another opening 78 diametrically opposite to the opening 70, allowing the passage of objects 2 through this crown 24, and located upstream and facing an upstream end 30a of the second conveyor 30 bringing these objects 2 towards the production isolator 32. This opening 78 is primarily used to allow extraction of the objects 2 out of the output rotatable conveyor 24.

The second conveyor 30 is also a gravity roller conveyor (or of another suitable type) ensuring automatic displacement of the objects 2 to be treated, substantially along the direction X.

Figure 3:
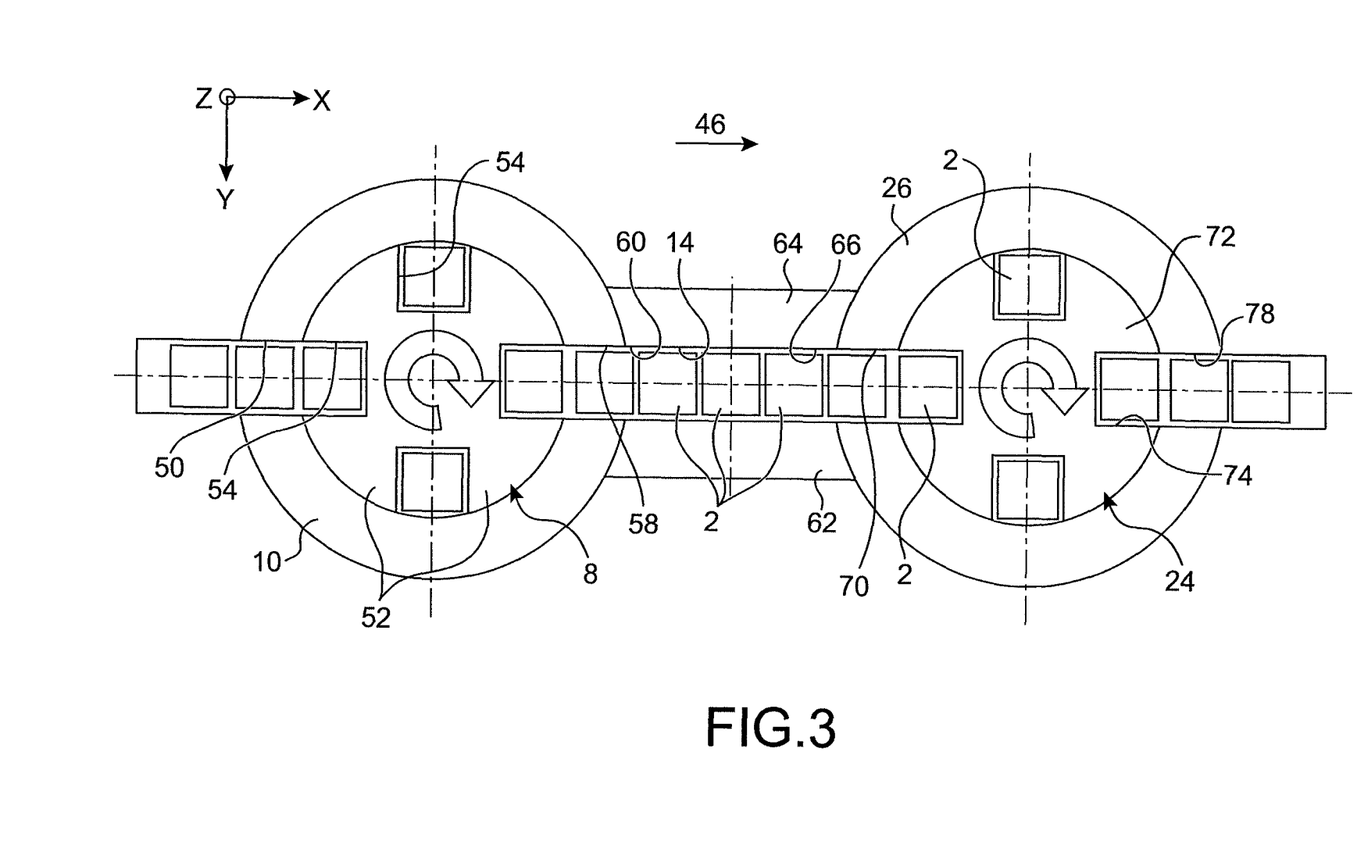
FIG. 3 shows a diagrammatic top view of the facility shown in FIGS. 1 and 2, intended to show the path of the objects within this facility.
Figure 4:
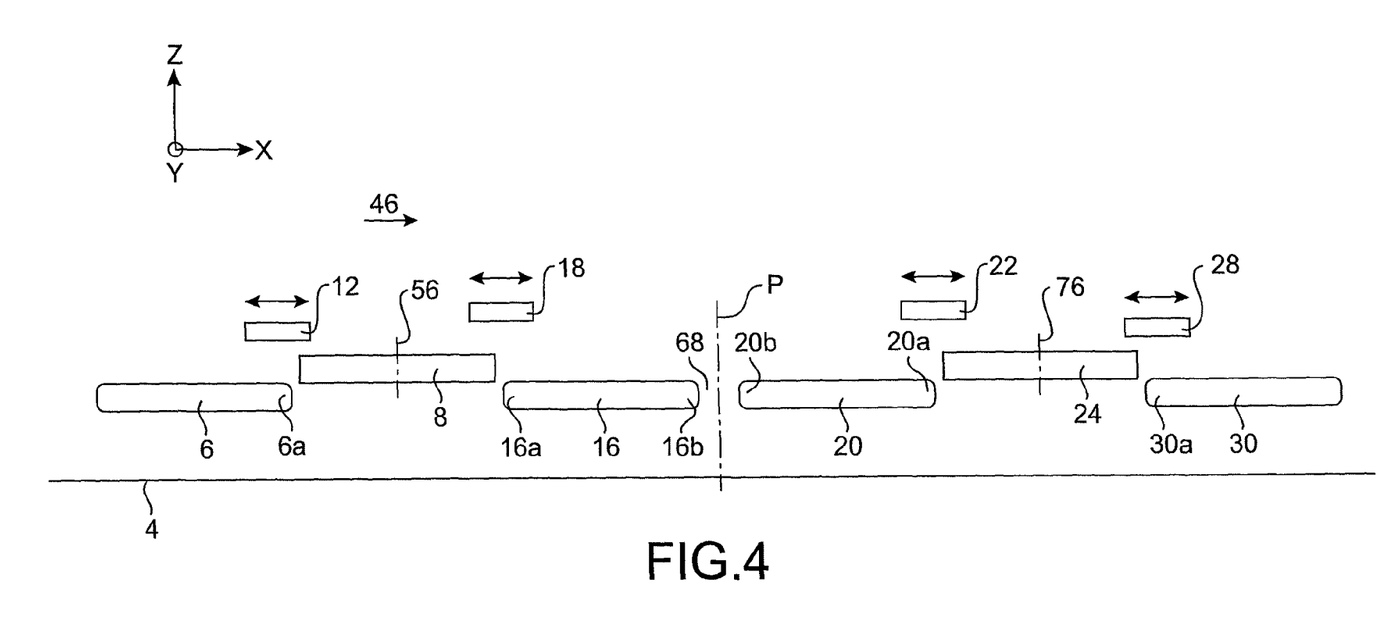
FIG. 4 shows a diagrammatic front view of the facility shown in FIGS. 1 and 2, intended to show the various means of moving the objects present within this facility.

Referring now more specifically to FIGS. 3 and 4, the path of a given object 2 through the facility 1 will be described.

First, the rotatable conveyor 8 is set into rotation around the axis 56 such that one of its housings 54 is placed facing the opening 50. Then, the first transfer means 12 is controlled so as to move in the X direction, the object 2 located the farthest downstream on the first conveyor 6, into the aforementioned housing 54, while passing through the opening 50.

The input rotatable conveyor 8 then completes two quarters of a revolution before presenting this object 2 facing the other opening 58. The second transfer means 18 is controlled so as to move, in the X direction, the object 2 into the inside of the processing chamber 14, while passing through the opening 58 and the inlet 60. It is understood that at each step of the rotatable conveyor 8, one object 2 has entered while another object 2 has exited, so as to optimize the pace.

Once this object has entered into this chamber 14, displacement of the object 2 in the direction X is automatically provided first by the internal input conveyor 16, and then by the internal output conveyor 20, these two conveyors being at a regulated speed. In this respect, it is noted that it is when the object 2 passes above the inter-conveyor space 68, i.e. when it simultaneously rests on the downstream end 16b and the upstream end 20b of the conveyors 16, 20, that it undergoes the most intense treatment, since it is then illuminated over 360° by the three electron beams which will be described hereafter.

Displacement of the object 2 on the regulated speed conveyor 20 is performed until this object 2 reaches the outlet 66, where this object 2 is able to cooperate with the third transfer means 22 controlled so as to move it in the X direction, right up to the inside of a housing 74 of the output rotatable conveyor 24, while passing through the outlet 66 and the opening 70 of the crown 26. To do this, the rotatable conveyor 24 is first set into rotation around its axis 76 such that one of its housings 74 is placed facing the opening 70.

When the object 2 is located in the housing 74, the output rotatable conveyor 24 then completes two quarters of a revolution before presenting this object 2 facing the other opening 78. The fourth transfer means 28 is then controlled so as to displace, in the X direction, the object 2 until it reaches the upstream end 30a of the second conveyor 30, while passing through the opening 78. Here again, it is understood that at each step of the rotatable conveyor 24, one object 2 has entered while another object 2 has exited, so as to optimize the pace.

Lastly, the object 2 is then automatically moved in the X direction by gravity on the conveyor 30, right up into the production isolator 32.

Naturally, as shown in FIG. 3, it is noted that the facility 1 is designed to be able to receive and hold several objects 2 simultaneously, implying that several of them are therefore laid out behind each other inside the treatment chamber 14. Another consequence, of course, lies in the fact that in operation, at each quarter revolution (each step) of the input rotatable conveyor 8, a new object 2 arrives facing the inlet 60 of the treatment chamber 14, before penetrating therein via the second transfer means 18.

As an indication, the rotatable conveyors 8, 24 may be associated with traditional electric motors to set them into rotation, while the elements 12, 18, 22, 28 may each assume the form of a stainless steel carriage mounted on a screw or ball, and actuated by a traditional electric motor. On the other hand, the elements 16 and 20 may each assume the form of a stainless steel chain link conveyor belt, and actuated by a traditional electric motor.

Figure 5:
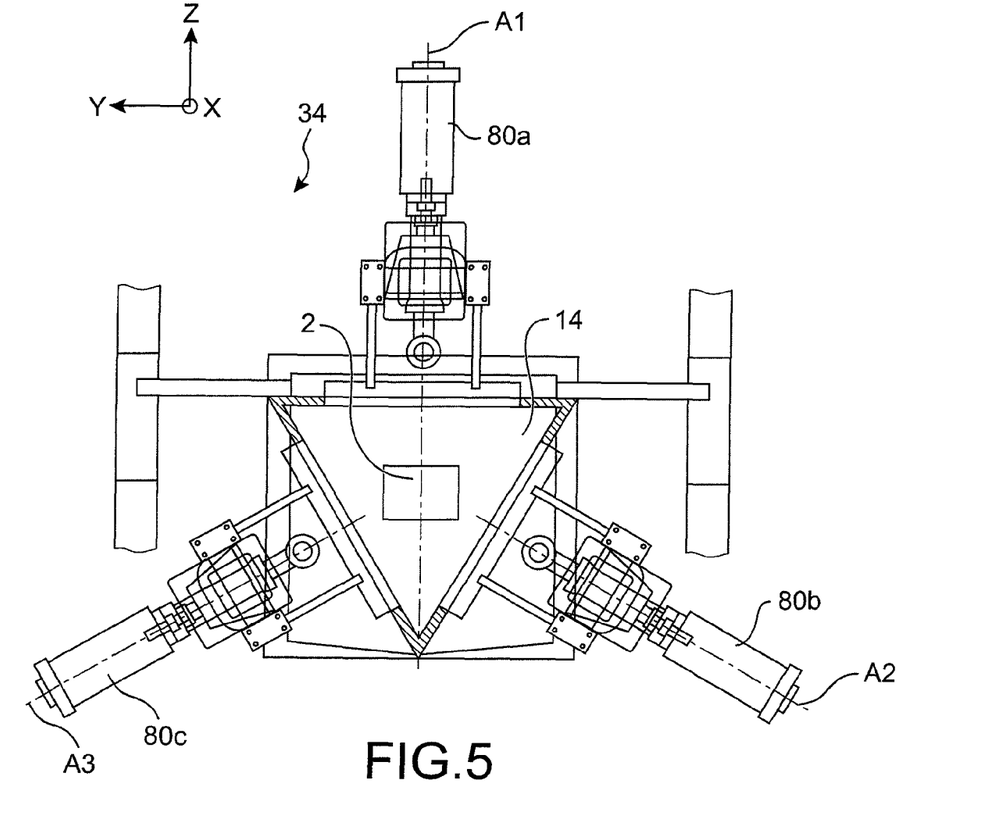
FIG. 5 shows a partial cross-sectional view along the V-V line of FIG. 1, intended to more specifically show the sterilization means of the facility.

With reference now to FIG. 5, showing the sterilizing means 34 presented in a preferred embodiment particularly well-suited to surface treatment of objects 2, it may be seen that the latter have three sources 80a, 80b, 80c each generating an electron beam along axes A1, A2, A3 respectively.

These axes are globally positioned at 120° relative to each other in a plane P shown in FIG. 4 and corresponding to the line V-V in FIG. 1. This plane P is orthogonal to the direction of forward motion of the objects 46, and crosses the inter-conveyor space 68 preferably in its middle. This is why the outer surface of an object 2 passing above this inter-conveyor space 68 is illuminated over 360°, through the combined action of the three sources 80a, 80b, 80c, the axes A1, A2, A3 of which preferably each cross this object 2 moving above the space 68.

Of course, various modifications may be made by one skilled in the art to the facility 1 for sterilizing objects by electron bombardment which has just been described solely as a non-limiting example.

The invention claimed is:

1. A facility for sterilizing objects by electron bombardment, comprising:
 a sterilization device including a treatment chamber having a linear path which moves the objects in a linear conveying direction, and three sources configured to generate an electron beam energy of 400 keV to 10 MeV, each source being positioned to generate an electron beam along a respective axis passing through the treatment chamber;
 a first conveyor and a second conveyor used for moving said objects and being respectively located on either side of said treatment chamber;
 an input rotatable conveyor designed for moving said objects and placed between the first conveyor and said treatment chamber;
 an output rotatable conveyor also designed for moving said objects and placed between said treatment chamber and the second conveyor, each of the input and output rotatable conveyors including both a plurality of radial projections laid out such that any two of the radial projections being directly consecutive to each other define a housing to receive an object and a casing surrounding the radial projections, the casing and the radial projections each comprising lead and arranged to create a radiation barrier such that radiation from the treatment chamber cannot pass between the casing and the radial projections, the object being able to be moved in said housing when a corresponding rotatable conveyor is set into motion, causing rotation of the housing; and a first transfer device configured to move the object located in the housing of the input rotatable conveyor which communicates with an inlet of said treatment chamber right up into the inside of the treatment chamber, said treatment chamber being equipped with a primary internal conveyor onto which the object may be brought by said first transfer device;

a second transfer device configured to move the object located inside said treatment chamber right up into the housing of the output rotatable conveyor which communicates with an outlet of this treatment chamber, said treatment chamber being equipped with a secondary internal conveyor from which the object may be moved into the housing of the output rotatable conveyor by said second transfer device, wherein a downstream end of the primary internal conveyor is located facing and away from an upstream end of the secondary internal conveyor so as to form an inter-conveyor space, the three axes each pass through the inter-conveyor space, and the primary internal conveyor is on an opposite side of the input rotatable conveyor from the first conveyor and the secondary internal conveyor is on an opposite side of the output rotatable conveyor from the second conveyor.

2. The facility for sterilizing objects according to claim 1, further comprising:

a third transfer device configured to move the objects located at a downstream end of the first conveyor into the housing of the input rotatable conveyor laid out facing this downstream end of the first conveyor.

3. The facility for sterilizing objects according to claim 2, further comprising:

a fourth transfer unit configured to move an object located in a housing of the output rotatable conveyor laid out facing an upstream end of the second conveyor right up onto this upstream end of the second conveyor.

4. The facility for sterilizing objects according to claim 1, wherein said primary internal conveyor has an upstream end located in proximity to the inlet of said processing chamber, and in that said secondary internal conveyor has a downstream end located in proximity to the outlet of said treatment chamber.

5. The facility for sterilizing objects according to claim 1, wherein said first conveyor, second conveyor, primary internal conveyor and secondary internal conveyor are each substantially rectilinear, and substantially positioned along a same straight line parallel to a direction of forward motion of the objects.

6. The facility for sterilizing objects according to claim 1, wherein said three axes are respectively positioned at 120° relative to each other in a plane P orthogonal to a direction of forward motion of the objects.

7. The facility for sterilizing objects according to claim 6, wherein said plane P passes through said inter-conveyor space.

8. The facility for sterilizing objects according to claim 6 or claim 7, wherein said sources are laid out such that each of the three axes passes through an object to be treated placed at the inter-conveyor space.

9. The facility for sterilizing objects according to claim 1, wherein said second conveyor opens into a production isolator into which the sterilized objects are brought.

10. The facility for sterilizing objects according to claim 1, wherein said input rotatable conveyor is placed in the casing having an opening facing the first conveyor to allow the introduction of objects into said input rotatable conveyor, and an opening located in the extension of the inlet of said treatment chamber, and upstream therefrom and in that said output rotatable conveyor is placed in the casing having an opening located in the extension of the outlet of said treatment chamber and downstream therefrom and an opening located facing the second conveyor to allow extraction of the objects from said output rotatable conveyor.

11. The facility for sterilizing objects according to claim 1, wherein the facility is configured to perform surface or core treatment of the objects to be treated.

12. The facility for sterilizing objects according to claim 1, wherein the casing and the radial projections of each of the input and output rotatable conveyors are made of lead.

13. The facility for sterilizing objects according to claim 1, wherein the first conveyor, the second conveyor, the primary internal conveyor, and the secondary internal conveyor all extend along a same axis.

* * * * *